US008820474B2

(12) United States Patent
Campbell et al.

(10) Patent No.: US 8,820,474 B2
(45) Date of Patent: Sep. 2, 2014

(54) EAR TIP PIECE FOR HEARING INSTRUMENTS

(75) Inventors: Don E. K. Campbell, Longwood, FL (US); William Chiu, Longwood, FL (US)

(73) Assignee: Magnatone Hearing Aid Corporation

( * ) Notice: Subject to any disclaimer, the term of this patent is extended or adjusted under 35 U.S.C. 154(b) by 362 days.

(21) Appl. No.: 13/199,309

(22) Filed: Aug. 25, 2011

(65) Prior Publication Data

US 2013/0051592 A1 Feb. 28, 2013

(51) Int. Cl.
*A61F 11/08* (2006.01)

(52) U.S. Cl.
USPC .......... 181/235

(58) Field of Classification Search
CPC ....... H04R 25/652; A61B 19/00; A61F 11/08
USPC .......... 181/135
See application file for complete search history.

(56) References Cited

U.S. PATENT DOCUMENTS

| | | | | |
|---|---|---|---|---|
| 2,487,038 | A * | 11/1949 | Baum | 181/135 |
| 3,050,056 | A | 8/1962 | Dressler | |
| 3,934,100 | A | 1/1976 | Harada | |
| 4,338,929 | A | 7/1982 | Lundin et al. | |
| D267,429 | S | 12/1982 | Harada | |
| 4,880,076 | A | 11/1989 | Ahlberg et al. | |
| 4,972,488 | A | 11/1990 | Weiss et al. | |
| 5,247,946 | A | 9/1993 | Holder | |
| 5,333,622 | A | 8/1994 | Casali et al. | |
| 5,824,968 | A | 10/1998 | Packard et al. | |
| 5,987,146 | A | 11/1999 | Pluvinage et al. | |
| 6,000,492 | A | 12/1999 | Puthuff et al. | |
| D419,675 | S | 1/2000 | Garcia | |
| D420,136 | S | 2/2000 | Barnard et al. | |
| D431,294 | S | 9/2000 | Barnard et al. | |
| 6,129,175 | A | 10/2000 | Tutor et al. | |
| 6,179,085 | B1 | 1/2001 | Brimhall et al. | |
| 6,275,596 | B1 | 8/2001 | Fretz et al. | |
| 6,359,993 | B2 | 3/2002 | Brimhall | |
| 6,513,621 | B1 | 2/2003 | Deslauriers et al. | |
| 6,532,295 | B1 | 3/2003 | Brimhall et al. | |
| 6,577,740 | B1 | 6/2003 | Bordewijk | |
| 6,691,822 | B2 * | 2/2004 | Meussen et al. | 181/135 |
| 6,801,629 | B2 | 10/2004 | Brimhall et al. | |
| D518,179 | S | 3/2006 | Holmes | |
| 7,013,016 | B2 | 3/2006 | Wolf | |
| 7,027,608 | B2 | 4/2006 | Fretz et al. | |
| 7,065,223 | B2 | 6/2006 | Westerkull | |
| 7,110,562 | B1 | 9/2006 | Feeley et al. | |
| 7,130,437 | B2 * | 10/2006 | Stonikas et al. | 381/322 |
| 7,240,765 | B2 | 7/2007 | Berg et al. | |

(Continued)

OTHER PUBLICATIONS

U.S. Appl. No. 11/040,763, filed Sep. 1, 2005, Fretz.

(Continued)

*Primary Examiner* — Forrest M Phillips
(74) *Attorney, Agent, or Firm* — Ice Miller LLP

(57) ABSTRACT

An ear tip piece device made of resilient material dimensioned for fitting the ear canal of a user, having a solid portion, a reversibly compressible portion and a first channel. In one embodiment, the ear tip piece is asymmetrical due to a bend. In another alternative embodiment, the ear tip piece has a second channel that is used for allowing natural transmission of sound to the ear.

22 Claims, 4 Drawing Sheets

(56) References Cited

U.S. PATENT DOCUMENTS

| | | | | |
|---|---|---|---|---|
| 7,298,858 | B2 * | 11/2007 | Wilson et al. | 381/328 |
| 7,313,245 | B1 | 12/2007 | Shennib | |
| 7,418,105 | B2 | 8/2008 | McIntosh | |
| 7,537,011 | B2 | 5/2009 | Falco | |
| 7,602,933 | B2 | 10/2009 | Cartwright et al. | |
| 7,864,972 | B2 | 1/2011 | McIntosh et al. | |
| 7,889,883 | B2 | 2/2011 | Cartwright et al. | |
| 7,899,200 | B2 | 3/2011 | Karamuk et al. | |
| 7,940,946 | B2 | 5/2011 | Caldarola | |
| 8,503,707 | B2 * | 8/2013 | Urso et al. | 381/328 |
| 2005/0082109 | A1 * | 4/2005 | Bordewijk | 181/135 |
| 2006/0147071 | A1 | 7/2006 | Neilson | |
| 2008/0276945 | A1 | 11/2008 | Rosen | |
| 2009/0067661 | A1 | 3/2009 | Keady et al. | |
| 2010/0084217 | A1 | 4/2010 | Blanchard | |

OTHER PUBLICATIONS

U.S. Appl. No. 11/031,915, filed Jul. 7, 2005, Gudmundsen et al.

U.S. Appl. No. 11/049,495, filed Aug. 3, 2006, Holmes.

U.S. Appl. No. 11/231,574, filed Nov. 16, 2006, Holmes.

International Search Report and Written Opinion for PCT/US12/00371, Nov. 19, 2012.

International Search Report and Written Opinion for PCT/US12/00370, Dec. 24, 2012.

* cited by examiner

EAR TIP PIECE FOR HEARING INSTRUMENTS

FIELD OF THE INVENTION

The present invention is directed to an ear tip piece comprising a solid portion and a reversibly compressible portion designed to conform to a person's ear canal and to be used in conjunction with hearing instruments, such as earphones, ear plugs, personal sound amplifiers, or the like.

BACKGROUND OF THE INVENTION

A semi-customized ear tip piece for insertion in an ear canal is disclosed that has a first end and a second end, wherein the first end includes a solid portion and the second end includes a reversibly compressible portion. A first channel is disclosed that passes through the solid portion for transmitting sound to the ear. In a preferred embodiment, the ear tip piece also has a bend. In an alternative embodiment, the solid portion comprises a base and a projection. The disclosed ear tip piece is preferably used in conjunction with various hearing instruments, such as Behind-the-ear ("BTE"), Over-the-ear ("OTE"), Receiver-in-canal ("RIC"), or Receiver and Microphone in canal hearing aids.

BTE or OTE hearing aids typically use an ear tip piece to locate and direct the amplified sound into the wearer's ear canal. RIC hearing aids use an ear tip piece as a holder to position the receiver or transducer in the ear canal. The majority of the ear tips currently on the market are of a symmetrical circular or oval shape with a round or dome shaped tip. It is important for acoustic reasons and for wearer comfort, to have the tip fit well.

Such known ear tip pieces are disclosed in U.S. Pat. No. 7,889,883 and U.S. Pat. No. 7,602,933, both issued to Cartwright et al. The ear tip pieces disclosed in the '883 and '933 patents have a generally cone-shaped appearance (or otherwise referred to as a "bullet-shape") and at the conical end, a central longitudinal passage is provided which can further be associated with various tube-like structures. The '883 and '933 patent ear tip pieces are comprised of material that is preferably a highly flexible and/or pliable material that can be compressed in a fashion so that distinct folds are formed in the material, creating what appears to be a "star-like" configuration when fully compressed along each fold line. The fold lines themselves can be depressions in the flexible material itself, physically scored into the material, or otherwise provided.

U.S. Pat. No. 7,027,608 issued to Fretz et al. discloses several embodiments of eartips. The '608 patent discloses a bud-shaped eartip that is a conically shaped member having a through bore for sound transmission and an interior socket configured to allow the bud-shaped eartip to be received on the honey dipper end of a tube. A flower-shaped eartip is disclosed that includes a central core and three flower petals extending from the central core. Each of the petals has a substantially ellipsoidal shaped end. The '608 patent discloses a variation of the flower eartip, the webbed flower eartip, in which the flower petals are connected by a thin web of eartip material. The webbed flower eartip will reduce the ambient sounds passage through the ear canal increasing occlusion. Another eartip disclosed in the '608 patent is the guppie-shaped eartip which includes a central body portion and a tail. The '608 patent also discloses a barb-shaped eartip including a central body portion and a barb extending from the central body portion. Another variation of an eartip disclosed in the '608 patent is a dome-shaped eartip having a bud-shaped core and a skirt starting about half way down the bud-shape and extending from the core. Yet another eartip variation disclosed in the '608 patent is a bud-shaped eartip having a wax flap.

SUMMARY OF THE INVENTION

An ear tip piece for insertion in an ear canal is disclosed that comprises a first end including a solid portion that is sized and shaped to be inserted into an ear canal, a second end including a reversibly compressible portion for sealing the ear canal, and a first channel passing through the solid portion for transmitting sound to the ear. In an alternative embodiment, the ear tip piece further comprises a bend between the first end and second end, wherein the bend is positioned to facilitate insertion of the ear tip piece at or near a first or second narrowing or bend of an ear canal when the first end is inserted into the ear canal. In a further alternative embodiment, the reversibly compressible portion is hollow. In another alternative embodiment, the solid portion comprises a base and a projection extending from the base, the first channel passing through the projection.

In an alternative embodiment, an ear tip piece for insertion in an ear canal is disclosed that comprises a first end including a solid portion that is sized and shaped to be inserted into an ear canal and a second end including a reversibly compressible portion for sealing the ear canal. The ear tip piece further comprises a bend between the first end and the second end, wherein the bend is positioned to facilitate insertion of the ear tip piece at or near a first or second narrowing or bend of an ear canal when the first end is inserted into the ear canal. The disclosed ear tip piece also comprises a first channel passing through the solid portion for transmitting sound to the ear, and a second channel passing through the solid portion for allowing natural transmission of sound to the ear drum.

DETAILED DESCRIPTION OF THE INVENTION

Figure 1:
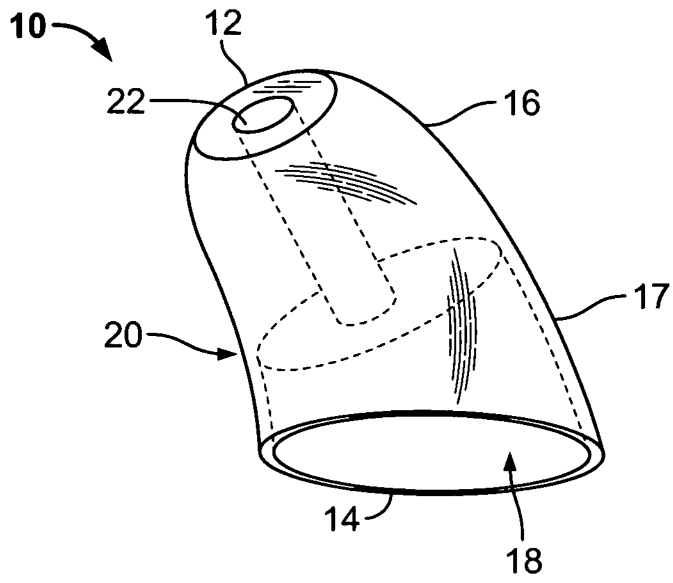
FIG. 1 is a perspective view of an ear tip piece according to one embodiment of the present invention, having a first channel for transmitting sound to the ear.
Figure 2:
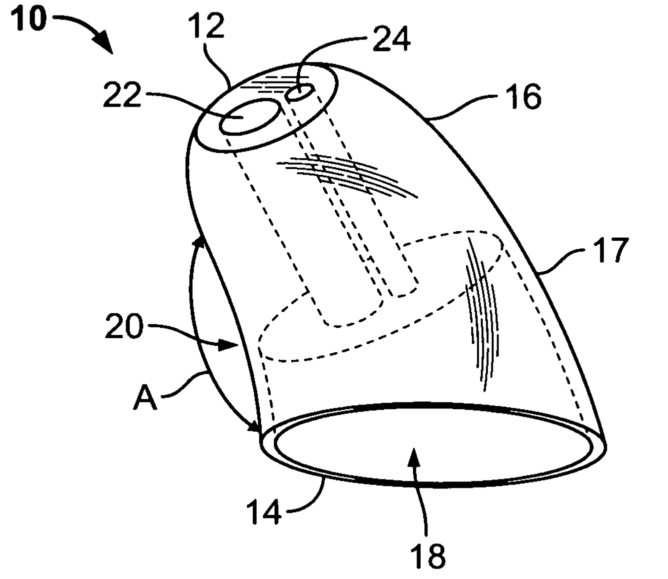
FIG. 2 is a perspective view of an alternative embodiment of an ear tip piece of the present invention, having a second channel used to allow the natural transmission of sound to the ear drum and pressure equalization.
Figure 3:
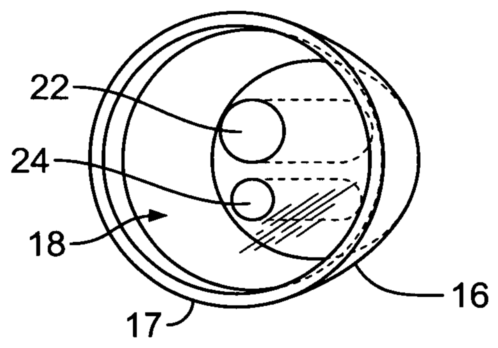
FIG. 3 is a rear perspective view of the ear tip piece of FIG. 2.

Referring to FIGS. 1-3, a left hearing aid ear tip piece 10 is shown having a first end 12 that includes a solid portion 16 that is sized and shaped to be inserted into an ear canal and a second end 14 that includes a reversibly compressible portion 17 that conforms to the shape of the ear canal to create a tight fit and secure the ear tip piece in the ear canal, and to seal the ear canal. In a preferred embodiment, the reversibly compressible portion 17 is hollow 18. In a further preferred embodiment, the ear tip 10 also has a bend 20. As best shown in FIG. 2, the bend 20 is preferably positioned between the first end 12 and the second end 14. The bend 20 begins at the second end 14 and becomes more pronounced as it moves to the first end 12. A first channel 22 is shown that passes through the solid portion 16 for transmitting sound to the ear. FIG. 2 shows a left ear tip piece having a second channel 24.

The ear tip piece is preferably made of a resilient material such as silicone or other materials known in the art, such as plastic, rubber, synthetic polymer or natural polymer. The ear tip piece is sized and shaped to be inserted within a human ear canal, which typically is elliptical in shape and has a smaller chord of between about 0.3 and 0.6 inches at the aperture of the ear canal. Between the first and second bends of the ear canal the smaller chord of the elliptical ear canal is generally from about 0.2 to 0.5 inches. In a preferred embodiment, the ear tip piece is approximately 0.48 inches long on the side having an interior curve with respect to the bend 20 and 0.59 inches on the opposite side. In an alternative embodiment, the ear tip piece is approximately 0.49 inches long on the side having an interior curve with respect to the bend 20 and approximately 0.60 inches on the opposite side. In a preferred embodiment, the ear tip piece is approximately 0.32 inches wide at the second end 14 and approximately 0.18 inches wide at the first end 12. In an alternative embodiment, the ear tip piece is approximately 0.36 inches wide at the second end 14 and approximately 0.27 inches wide at the first end 12.

The ear tip piece is inserted into a person's ear canal such that it is positioned close to the ear drum, preferably near or beyond the first or second sloping and/or narrowing of the ear canal, also referred to in the art as a bend. The shape of the disclosed ear tip piece preferably includes a bend 20. In a preferred embodiment, the bend forms an interior angle A of approximately 72°+/−15°. The bend 20 is preferably positioned and shaped to allow the ear tip piece to more closely approximate the shape of the ear canal, facilitating deeper insertion into the ear canal than can be accomplished with previous ear tip pieces, such as conventional dome shaped ear tip pieces. This allows the ear tip piece to be positioned closer to the ear drum, thereby reducing the air volume or acoustic mass present between the end of the ear tip piece and the ear drum. This air volume or acoustic mass must be moved during sound transmission to enable a person to hear. The smaller the acoustic mass, the less air volume that must be moved, which improves the wearer's hearing experience and comfort and lowers the corresponding hearing device amplification required to increase the sound pressure level at the ear drum. In addition, forming the first and second channels within the solid portion allows the channels to have a fixed angle relative to the ear tip piece, thereby permitting the channels to be more accurately directed toward the ear drum.

The solid portion 16 of the ear tip piece 10 provides a more rigid structure that helps the wearer properly align the ear tip piece in the ear canal. In a preferred embodiment, the solid portion 16 extends approximately 0.35 inches from the first end 12 toward the second end 14. The more rigid structure also provides tactile feedback to the wearer while the ear tip piece is being inserted into the ear canal, providing the wearer with the feeling that the device is traversing fully into the ear canal, is properly seated and will not fall out.

The solid portion 16 of the ear tip piece 10 also directs sound—such as sound produced by a conventional hearing aid speaker or receiver, as detected by a transducer and as transmitted through tubing fitted into the first channel 22—substantially toward the ear drum and not substantially into the side wall of the ear canal. In a preferred embodiment, this is partially accomplished via the bend 20 and the flexible nature of the reversibly compressible portion 17, which allows the ear tip piece to be compressed. This allows the ear tip piece to better follow the natural curve of the ear, which, when used in conjunction with a hearing aid, essentially guides the speaker or receiver, tubing, and/or coupler along the axis of the ear canal. Sounds delivered directly at the ear drum increase transmission efficiency to the middle ear system and improve a wearer's hearing. Conventional dome style tips or flaccid tips do not provide any guidance in positioning the receiver towards the ear drum at a proper angle and more effort has to be applied to shaping of the wire system, which is cumbersome due to the delicate wires and risk of breaking the contact points and causing a short in the wire.

Once inserted into the ear canal, the reversibly compressible portion 17 expands to conform to the shape of the ear canal, which secures the ear tip piece within the ear canal and creates a substantially tight seal within the ear canal. As can be seen in FIGS. 1-3, the second end 14 flares outward, such that it is wider than the first end 12. This also helps create a more effective seal of the ear canal. In some cases, a completely airtight sealing of the aperture of the ear canal may result in an occlusion effect, which causes an altered perception of one's voice while talking. By fitting deeper in the ear canal the ear tip piece takes up more space relative to the size of the ear canal and prevents a wearer's throat generated vocals from entering the ear canal by sealing off the cartilaginous portion where larynx generated transmissions enter the ear canal. Some wearers find this characteristic to be beneficial by reducing the occlusion effect, also described as "head in a barrel" or echo complaints and restoring a more natural sound to their voice.

The tight seal created by the reversibly compressible portion 17 of the ear tip piece also results in greater comfort and security to the wearer, by, for example, minimizing or eliminating vibrations caused by walking or other wearer movements. In a preferred embodiment where the ear tip piece is used in conjunction with a hearing device, when vibrations reach the hearing device through either the tubing or wire they can adversely affect sound quality and may cause or increase the tickle effect. The tickle effect generally occurs when only a few of the hairs that line the ear canal are engaged or contacted by an object, such as an ear tip piece. However, if a large surface area and a resultant large number of hairs are all pressed at the same time, the tickle effect is minimized or eliminated. The solid portion 16 and reversibly compressible portion 17 of the disclosed ear tip piece may be configured to create a substantial contact surface with the surface of the ear canal, reducing the tickle effect felt by a wearer.

In a preferred embodiment, the reversibly compressible portion 17 is formed by a hollow 18 that has relatively thin walls that facilitate compression and adaptation of the reversibly compressible portion to the shape of the ear canal. In a particularly preferred embodiment, the walls of hollow 18 range in thickness from about 0.03 inches to 0.05 inches thick and, in an alternative embodiment, range from about 0.05 inches to 0.07 inches thick. In a particularly preferred embodiment, the walls of the hollow 18 of reversibly compressible portion 17 are approximately 0.02 inches thick. The size of the hollow 18 reversibly compressible portion 17 is may be adjusted to fit an individual ear by trimming. For example, the hollow 18 reversibly compressible portion 17 may be trimmed using a pair of scissors or any other suitable means, to remove any portion of the ear tip piece that protrudes outside of a wearer's ear canal. This enables the ear tip piece to be customized to an individual wearer.

As shown in FIG. 1, a first channel 22 allows sound transmission between the ear drum and an environment outside the ear. Alternatively, the first channel 22, in FIG. 1 can be used to fit a speaker or receiver of a hearing aid system, used to deliver amplified sound to the ear drum.

FIG. 2 depicts a further embodiment that also has a second channel 24. The second channel 24 may be used for venting, which allows natural transmission of unamplified sound between the ear drum of a wearer and an environment outside the ear, as occurs when no ear tip piece or hearing device is inserted into the wearer's ear canal. This tends to help alleviate the occlusion effect, where a wearer's voice sounds altered and possibly echoes, by allowing sound to traverse naturally to and from the ear. When used in conjunction with a hearing aid, such venting may vary the gain in the ear canal created by the amplified sound produced by the speaker or receiver. The unamplified natural sound transmitted through the second channel 24, depicted as a vent in FIG. 2, may combine with the amplified sound, which may either constructively and/or destructively interfere with the unamplified vented sound. Altering the width of the vent can reduce, in many cases, the amount of feedback or whistling that may occur as a result of the amplified sound looping back to the microphone or transducer of the hearing aid and, in other cases, can make the hearing aid sound warmer due to the increased amplification achieved. The warmer or improved sound quality is typically achieved by either lessening the occlusive effect experienced by the wearer or by increasing the insertion loss or seal created by the ear tip piece, resulting in increased amplification. The size of the second channel 24 can be adjusted by adding a separate vent plug (not shown) that changes the width of the channel.

Figure 6:
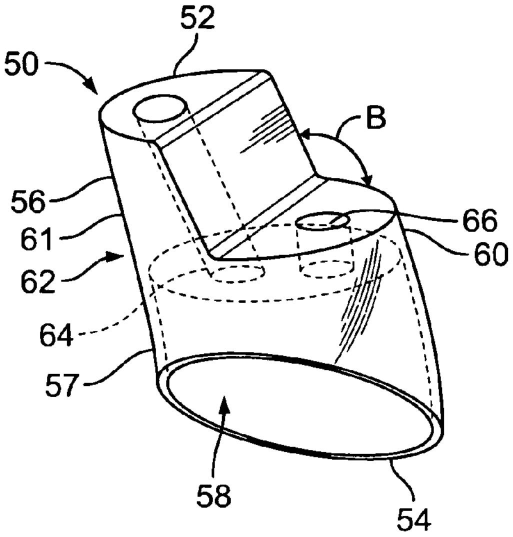
FIG. 6 is perspective view of another alternative embodiment of an ear tip piece of the present invention having a solid portion that has a base and a projection.

The first channel 22 and the second channel 24 can be a variety of widths, shapes, or slopes to allow for various tubes, receivers and monitors to be fit therein by friction or other known methods. In an embodiment, the width of the first channel 22 ranges from approximately 0.06 inches to 0.13 inches and in a preferred embodiment is approximately 0.10 inches wide. In a further embodiment, the second channel 24 ranges in width from about 0.02 inches to 0.13 inches and in a preferred embodiment is approximately 0.09 inches wide. The first and second channels may be parallel or arranged at different angles to each other, as best shown in FIG. 6. For example, the slope of the first channel 22 may be designed to direct the transmission of sound toward a wearer's ear drum. The first and/or second channel may have threaded interior surfaces to facilitate coupling to various sized tubes, receivers and monitors.

In an alternative embodiment, the second channel 24 may be used to insert a probe microphone to perform a real ear hearing test on a wearer while using a hearing aid. The probe microphone measurement or real ear measurements allow the function of a hearing aid to be tested while it is being worn. The results of the real ear hearing test allow adjustments to be made to ensure optimal amplification of sound when the hearing aids are being worn. Such real ear measurements can be used to identify variations caused by the anatomy of the particular wearer.

FIG. 3 depicts a rear view of the ear tip piece, showing the solid portion 16, the reversibly compressible portion 17, a first channel 22 and a second channel 24. In FIG. 3, the reversibly compressible portion 17 of the embodiment is hollow 18 and oval-shaped in cross-section. The oval shape and flare of the reversibly compressible portion 17 facilitates the adaptation to the shape and creation of a seal within the ear canal.

In an alternative embodiment, the second end 14 that includes the reversibly compressible portion 17 is oval shaped in cross-section, such as an ellipse, to more closely conform to the shape of the ear canal. In a preferred embodiment, the second end 14 is elliptical shaped in cross-section, the short chord of the ellipse ranging from about 0.31 inches to about 0.36 inches and the long chord of the ellipse ranging from about 0.49 inches to about 0.59 inches, +/−0.05 inches. In a particularly preferred embodiment, the short chord of the elliptical cross-section of second end 14 is about 0.31 inches and the long chord is about 0.50 inches, +/−0.05 inches. In an alternative particularly preferred embodiment, the short chord of the elliptical cross-section of the second end 14 is about 0.36 inches and the long chord is about 0.59 inches, +/−0.05 inches.

In an alternative embodiment, the first end 12 is oval shaped in cross-section. In a preferred embodiment, the first end 12 is elliptical in cross-section, the short chord of the ellipse ranging from about 0.18 inches to about 0.27 inches and the long chord of the ellipse ranging from about 0.26 inches to about 0.36 inches, +/−0.05 inches. In a particularly preferred embodiment, the short chord of the elliptical cross-section of the first end 12 is about 0.18 inches and the long chord is about 0.26 inches, +/−0.05 inches. In an alternative embodiment, the short chord of the elliptical cross-section of the first end 12 is about 0.27 inches and the long chord is about 0.36 inches, +/−0.05 inches.

Figure 4:
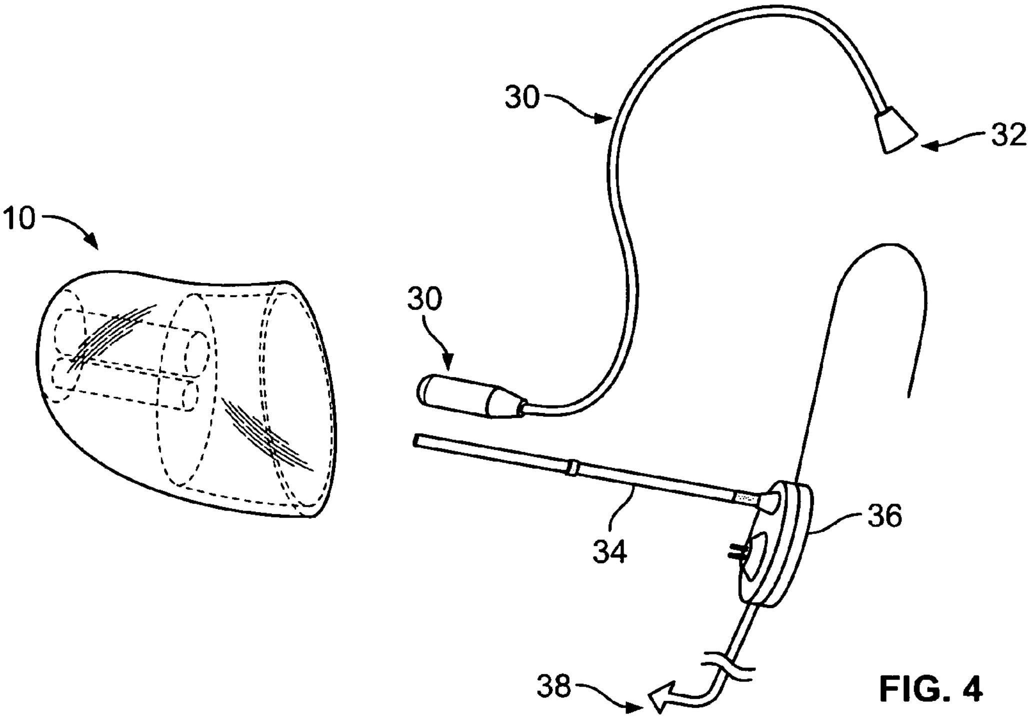
FIG. 4 is a schematic view of an application for using the ear tip piece of FIG. 2 with RIC (receiver in canal) hearing aid unit and real ear measurement probe tube thereof.

FIG. 4 depicts an embodiment of a left ear tip piece 10 being used with an RIC hearing aid. The speaker or receiver 30 is positioned inside the first channel, e.g. sized and shaped to friction fit within the channel, in the ear tip piece and connected to a RIC hearing aid via a connector 32. In a two channel embodiment, as shown in FIG. 4, a probe tube 34 is positioned inside a second channel and attached to a probe microphone 36. Probe microphone or real ear measurements received from the probe microphone 36 are sent to a monitor system 38 to enable an audiologist to assess the functionality of a wearer's hearing aids as is known in the art.

Figure 5:
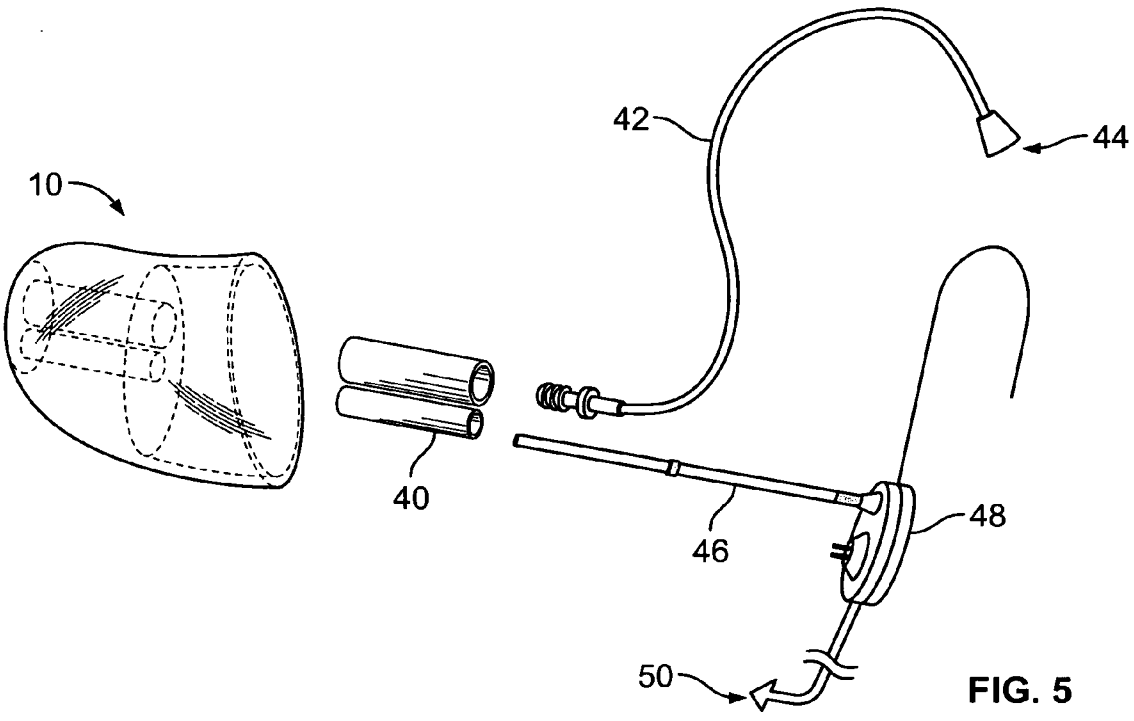
FIG. 5 is a schematic view of an application for using the ear tip piece of FIG. 2 with OTE (over the ear) thin tube used in conjunction with a hearing aid and real ear measurement probe tube thereof and coupler.

Similarly, FIG. 5 depicts an embodiment of a left ear tip piece 10 being used with an OTE or BTE hearing aid. In this embodiment a coupler 40 is used to adjust the width of the first channel to allow connection of a thin tube 42 to the ear tip piece 10. The thin tube 42 is then connected to an OTE/BTE hearing aid via a connector 44. The coupler 40 may also be used to connect the probe tube 46 to the ear tip piece 10. The probe microphone 48 is connected to the probe tube 46 and sends data to a monitor system 50.

The coupler 40 is preferably made of a more rigid material than the ear tip piece, such as plastic, and functions to narrow the width of the first channel and/or second channel to enable various tubes or other items to be coupled to the ear tip piece. The coupler 40 may be fixed within the channel by glue, friction fit, or fit via a barbed interface. In a preferred embodiment, the coupler 40 is a tubular piece of rigid material, preferably cylindrical, having a channel extending through the center and having barbs on the exterior surface to allow it to be fit inside a single channel in the ear tip piece. In an alternative embodiment, the coupler (not shown) comprises two of the tubular pieces described above that are joined together at an outer surface and configured to be inserted inside both channels of a two channel embodiment of the ear tip piece. In addition, the interior surface of the coupler's channel may be provided with threads (not shown) to facilitate coupling of a device, such as a hearing aid, to the coupler and insertion of the coupler and device into the ear tip piece channel. Couplers can come in a variety of materials, shapes and sizes. By having a variety of couplers available for use when coupling different materials and/or devices to the ear tip piece, this allows the same ear tip piece to be used with a variety of hearing aids or other systems, resulting in a reduction in inventory.

In a preferred embodiment, the ear tip piece is easily removed from the receiver or tubing inserted into the first or second channel, as, for example, shown in FIGS. 4 and 5, and is washable.

Figure 8:
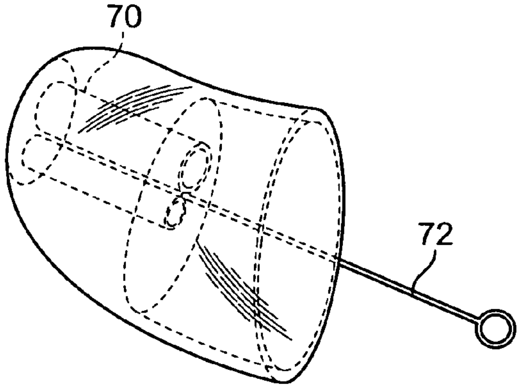
FIG. 8 is a perspective view of yet another alternative embodiment of an ear tip piece of the present invention showing couplers inserted in the first and second channels and an extraction string coupled to the couplers.

In an alternative embodiment of a left ear tip piece shown in FIG. 8, a coupler 70 may also be used to facilitate coupling of an extraction device, such as an extraction string 72, system, or lanyard. In a preferred embodiment, the extraction string is made of any suitably strong, thin material, such as fishing wire or a filament. The extraction string 72 may be fixed to the coupler 70 by gluing or other methods known in the art.

Figure 7:
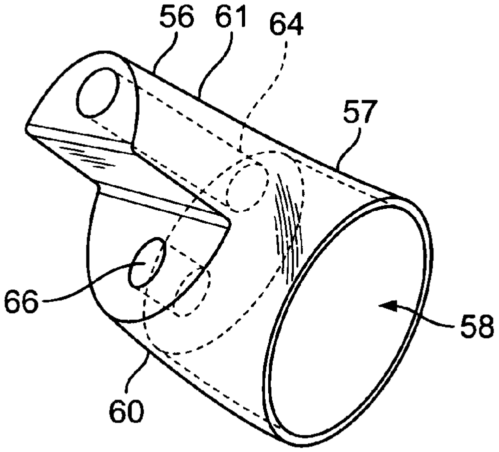
FIG. 7 is a top perspective view of an alternative embodiment of the ear tip piece of FIG. 6 having a base and a projection positioned at a different angle.

FIGS. 6 and 7 show an alternative embodiment of the ear tip piece 50, having a first end 52 including a solid portion 56 that is sized and shaped to be inserted into an ear canal and a second end 54 including a reversibly compressible portion 57 for sealing the ear canal. FIG. 6 shows a left ear tip piece and FIG. 7 shows a right ear tip piece. In the embodiment depicted in FIGS. 6 and 7 the reversibly compressible portion 57 is hollow 58. The ear tip piece 50 has a bend 62 between the first end 52 and the second end 54. The bend 62 extends upward from the second end 54 to the first end 52. The ear tip piece also has a first channel 64 and a second channel 66. In this embodiment, the solid portion 56 comprises a base 60 and a projection 61 that are positioned at an angle to one another B. Different angles between base 60 and a projection 61 may be used to better adapt the ear tip piece to the contour of the ear canal and/or direct the first channel toward the ear drum, as illustrated by comparison of FIGS. 6 and 7. In a preferred embodiment shown in FIG. 6, the base 60 and projection 61 form an interior angle B of about 105°+/−15°. The projection 61 extends from the base and the first channel 64 passes through the projection. The projection 61 of the solid portion 56 has a narrower width than the base 60 and is preferably just large enough to cover a speaker or receiver unit, tubing, coupler, or other material inserted in the first channel 64. This provides the smallest sized ear tip piece 50 and allows the ear tip piece to be inserted at the deepest and most narrow shape of the canal.

The base 60 and projection 61 ear tip piece embodiment reduces the occlusion effect by using less solid mass in the ear canal, and it provides less mass at the tip of the device where many ear canals begin to narrow. This increases the percentage of ear canals that can be fit. Further, the base 60 and projection 61 create an angle that facilitates the insertion of the ear tip piece into the ear canal as it follows the contour of the ear towards the ear drum. This angle allows the ear tip piece to follow the contour deeper into the ear canal than conventional ear tip pieces.

The embodiment shown in FIG. 6 provides a second channel 66 used for venting, discussed above, which remains unobstructed thereby reducing the occlusive effect. The second channel 66 passes through the base 60. When the venting channel is left unobstructed, unamplified sound can reach the eardrum directly, and improve the natural sound quality heard by patients with normal or mild hearing loss in the low frequencies. Simultaneously, the total acoustic mass of the ear canal has still been reduced (effective ear canal volume has been decreased) causing corresponding insertion loss. The tradeoff benefit to insertion loss, is the fact that less air pressure is required to reach the same levels of gain, increasing the added stable gain.

Figure 9:
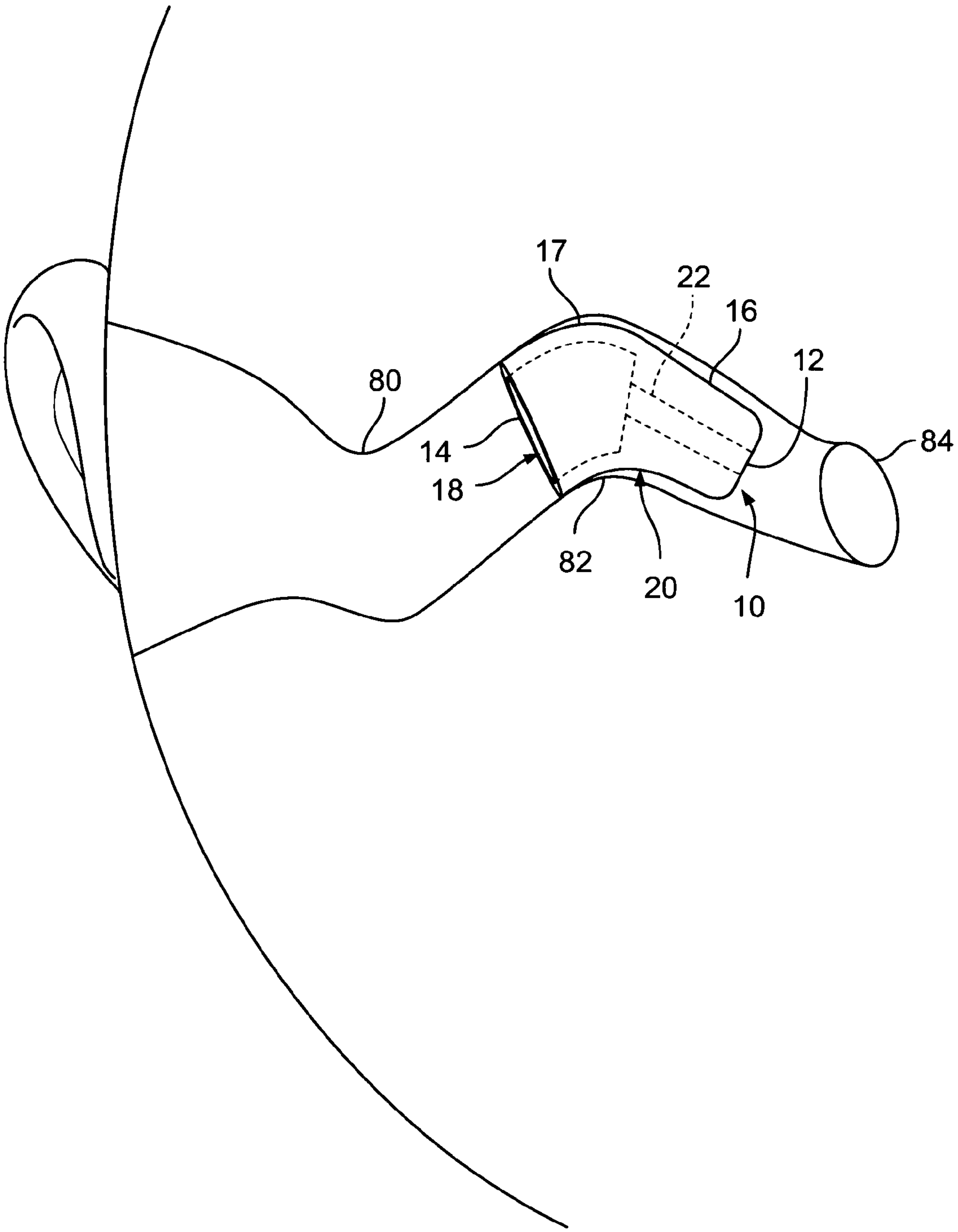
FIG. 9 is a top view of a human ear canal showing an embodiment of an ear tip piece inserted into the ear canal.

FIG. 9 depicts a right ear tip piece 10 inserted into a human ear canal, shown from a top view, having a first bend 80 and a second bend 82. The ear tip piece 10 has a first end 12 including a solid portion 16 sized and shaped to be inserted into an ear canal and a second end 14 including a reversibly compressible portion 17 for sealing the ear canal. The depicted ear tip piece 10 has a bend 20 for facilitating insertion of the ear tip piece and a first channel 22 for transmitting sound to the ear. The reversibly compressible portion 17 is preferably hollow 18. As shown in FIG. 9, the reversibly compressible portion 17 becomes compressed against the walls of an ear canal, adapting to the shape of the ear canal to create a seal.

Bend 20 is preferably positioned and shaped to facilitate insertion of the ear tip piece at or near the first bend 80 or, alternatively, the second bend 82. The ear tip piece 10 shown in FIG. 9 is inserted at or near the second bend 82 in close proximity to the ear drum 84. The positioning of the ear tip piece 10 in close proximity to the ear drum 84 reduces the size of the acoustic mass or air volume that must be moved to stimulate the ear drum, resulting in an improved hearing experience for the wearer and, when used with a hearing aid, reducing the amplification required to increase the sound pressure level at the ear drum. Because first channel 22 is formed in solid portion 16, its angle relative to the ear tip piece is fixed, allowing the first channel to be directed at ear drum 84.

Those of skill in the art will appreciate that, in addition to being used with RIC, OTE or BTE hearing aids, the claimed ear tip piece can be adapted for use in conjunction with stethoscopes, MP3/IPOD/Digital audio players, or sound recording devices. The ear tip piece can also be used with a sound blocking ear plug or a swimmer's ear plug.

While various embodiments have been described, it will be apparent to those of ordinary skill in the art that many more embodiments and implementations are possible within the scope of the invention. Accordingly, the invention is not to be restricted except in light of the attached claims and their equivalents.

What is claimed is:

1. An ear tip piece for insertion in an ear canal, comprising:

a first end including a solid portion that is sized and shaped to be inserted into and align the ear tip piece in an ear canal;

a second end including a reversibly compressible portion for sealing the ear canal; and a first channel formed in the solid portion for transmitting sound to the ear.

2. The ear tip piece of claim 1, further comprising a bend between the first end and second end, wherein the bend is positioned and shaped to facilitate insertion of the ear tip piece at or near a first or second bend of the ear canal.

3. The ear tip piece of claim 2, wherein the bend forms an angle in a range from about 57° to about 87°.

4. The ear tip piece of claim 1, wherein the reversibly compressible portion is hollow.

5. The ear tip piece of claim 4, wherein the size of the hollow reversibly compressible portion is adjustable to fit an individual ear by trimming.

6. The ear tip piece of claim 1, further comprising a coupler inserted into the first channel for changing the width of the first channel.

7. The ear tip piece of claim 1, further comprising a second channel passing through the solid portion.

8. The ear tip piece of claim 7, wherein the first channel and second channel are parallel to each other.

9. The ear tip piece of claim 7, wherein the first channel and second channel are at different angles to each other.

10. The ear tip piece of the claim 7, further comprising a plug inserted into the second channel for changing the width of the second channel.

11. The ear tip piece of claim 1, wherein the solid portion comprises a base and a projection extending from the base, the first channel passing through the projection.

12. The ear tip piece of claim 11, further comprising a second channel passing through the base.

13. The ear tip piece of claim 11, wherein the projection and the base form an angle of 105°+/−15°.

14. The ear tip piece of claim 1, further comprising a receiver inserted into the first channel.

15. The ear tip piece of claim 1, further comprising a sound tube inserted into the first channel.

16. The ear tip piece of claim 1, wherein the first channel has a threaded interior surface.

17. The ear tip piece of claim 1, further comprising a coupler inserted into the first channel or second channel for reducing the width of the channel, the coupler including an extraction device to facilitate remove of the ear tip piece from the ear.

18. The ear tip piece of claim 1, wherein the second end is oval shaped in cross-section.

19. The ear tip piece of claim 18, wherein the second end is elliptical shaped in cross-section, having a short chord ranging from about 0.31 inches to about 0.36 inches and a long chord ranging from about 0.49 inches to about 0.59 inches.

20. An ear tip piece for insertion in an ear canal, comprising:

a first end including a solid portion that is sized and shaped to be inserted into and align the ear tip piece in an ear canal;

a second end including a reversibly compressible portion for sealing the ear canal;

a bend between the first end and the second end, wherein the bend is positioned and shaped to facilitate insertion of the ear tip piece at or near a first or second bend of an ear canal when the first end is inserted into the ear canal;

a first channel formed in the solid portion for transmitting sound to the ear; and a second channel formed in the solid portion for allowing natural transmission of sound to the ear.

21. The ear tip piece of claim 20, wherein the solid portion comprises a base and a projection extending from the base, the first channel passing through the projection and the second channel passing through the base.

22. An ear tip piece for insertion in an ear canal, comprising:

a first end including a solid portion that is sized and shaped to be inserted into and align the ear tip piece in an ear canal, wherein the solid portion comprises a base and a projection extending from the base;

a second end including a reversibly compressible portion for sealing the ear canal;

a bend between the first end and the second end, wherein the bend is positioned and shaped to facilitate insertion of the ear tip piece at or near a first or second bend of an ear canal when the first end is inserted into the ear canal;

a first channel formed in the projection for fitting a receiver to deliver amplified sound to the ear; and a second channel formed in the base for allowing natural transmission of sound to the ear.

* * * * *